(12) United States Patent
Kinzie et al.

(10) Patent No.: US 8,074,499 B2
(45) Date of Patent: Dec. 13, 2011

(54) METHOD AND SYSTEM FOR DETECTING A CRACK ON A TURBOMACHINE BLADE

(75) Inventors: Kevin W. Kinzie, Moore, SC (US);
Chingwei M. Shieh, Mechanicville, NY (US); Dongjai Lee, Greer, SC (US)

(73) Assignee: General Electric Company, Schenectady, NY (US)

( * ) Notice: Subject to any disclaimer, the term of this patent is extended or adjusted under 35 U.S.C. 154(b) by 153 days.

(21) Appl. No.: 12/644,327

(22) Filed: Dec. 22, 2009

(65) Prior Publication Data

US 2011/0150626 A1 Jun. 23, 2011

(51) Int. Cl.
*G01N 29/04* (2006.01)
(52) U.S. Cl. ...................... 73/112.01; 73/660
(58) Field of Classification Search ............... 73/112.01, 73/660
See application file for complete search history.

(56) References Cited

U.S. PATENT DOCUMENTS

| | | | | |
|---|---|---|---|---|
| 4,408,294 A * | 10/1983 | Imam | | 702/35 |
| 4,685,335 A * | 8/1987 | Sato et al. | | 73/660 |
| 4,732,532 A | 3/1988 | Schwaller et al. | | |
| 5,152,172 A | 10/1992 | Leon et al. | | |
| 5,445,027 A * | 8/1995 | Zorner | | 73/593 |
| 6,487,909 B2 * | 12/2002 | Harrold et al. | | 73/593 |
| 6,536,284 B2 | 3/2003 | Bonanni | | |
| 6,629,463 B2 | 10/2003 | Naudet et al. | | |
| 6,659,712 B2 | 12/2003 | Brooks et al. | | |
| 7,536,457 B2 * | 5/2009 | Miller | | 709/224 |
| 7,555,951 B2 * | 7/2009 | Shadman et al. | | 73/579 |
| 2005/0171736 A1 | 8/2005 | Kang | | |
| 2007/0260363 A1 * | 11/2007 | Miller | | 701/2 |
| 2007/0272018 A1 | 11/2007 | Shadman et al. | | |
| 2010/0161255 A1 * | 6/2010 | Mian et al. | | 702/56 |

FOREIGN PATENT DOCUMENTS

| | | |
|---|---|---|
| EP | 0599863 A1 | 6/1994 |
| WO | 8201416 A1 | 4/1982 |
| WO | 9304365 A1 | 3/1993 |
| WO | 2008093349 A1 | 8/2008 |
| WO | 2010102876 A2 | 9/2010 |

OTHER PUBLICATIONS

GB Search Report issued in connection with corresponding GB Application No. GB1021121.7, Mar. 18, 2011.

* cited by examiner

*Primary Examiner* — Freddie Kirkland, III
(74) *Attorney, Agent, or Firm* — Dale J. Davis; Ernest G. Cusick; Frank A. Landgraff

(57) ABSTRACT

Embodiments of the present invention may provide real-time monitoring of a compressor section to determine the possibility of a crack forming on a rotating blade. The present invention does not require the shutdown of the machine. The present invention may be configured to automatically raise an alarm if the acoustic signature of the compressor changes in way that may be consistent with the cracking of a blade.

18 Claims, 4 Drawing Sheets

METHOD AND SYSTEM FOR DETECTING A CRACK ON A TURBOMACHINE BLADE

BACKGROUND OF THE INVENTION

The present invention relates generally to a compressor section of a turbomachine; and more particularly to a method of detecting a potential crack on a blade of the compressor section.

Turbomachine, such as, air-breathing combustion turbines, have a compressor section with a plurality of blades arrange in multiple rotor stages. During normal operation, the tip speed of these blades may be at sonic or supersonic speeds. A crack in a blade may severely damage the entire turbomachine, if that blade liberates during normal operation.

Currently known methods of crack detection are normally performed through a static inspection process, while the turbomachine is offline. However, these methods require the shutdown of the turbomachine. Here, turbomachine operators are reluctant to stop the operation of the turbomachine.

Therefore, there is a desire for an improved method for detecting a crack on the blade. The method should be capable of detection a possible crack while the turbomachine operates, allowing the turbomachine to operate longer between offline inspections for blade cracking.

BRIEF DESCRIPTION OF THE INVENTION

In an embodiment of the present invention, a method of detecting a possible crack on a blade located within a compressor section of a turbomachine, the method comprising: providing a turbomachine comprising: a compressor section, wherein the compressor section comprises a plurality of blades; and an acoustic detection device configured for monitoring the compressor section as the turbomachine operates, wherein the acoustic detection device receives acoustic data relating to the plurality of blades; utilizing the acoustic data to generate an acoustic signature corresponding to the plurality of blades; and determining whether the acoustic signature is within an acceptable range; wherein a determination that the acoustic signature is outside of the acceptable range indicates a likelihood of a crack on at least one of the plurality of blades.

In an alternate embodiment of the present invention, a method of monitoring a turbomachine for a formation of a crack on a blade of the turbomachine, the method comprising: providing a turbomachine comprising a plurality of blades; and an acoustic detection device configured for monitoring the turbomachine during operation, wherein the acoustic detection device receives acoustic data relating to the plurality of blades; utilizing the acoustic data to generate an acoustic signature corresponding to the plurality of blades; comparing the acoustic signature with a related acoustic signature; determining whether the acoustic signature is within an acceptable range; and generating a notification on a result of determining whether the acoustic signature is within an acceptable range of the related acoustic signature; wherein a determination that the acoustic signature is outside of the acceptable range indicates that a crack on at least one of the plurality of blades is possible.

In an another alternate embodiment of the present invention, a system for detecting an existence of a crack on a blade within a gas turbine, the system comprising: a gas turbine comprising a plurality of blades; an acoustic detection device configured for monitoring operation of the gas turbine, wherein the acoustic detection device receives acoustic data relating to the plurality of blades and is located adjacent the compressor section; a control system, wherein the control system performs the steps of: utilizing the acoustic data to generate an acoustic signature corresponding to the plurality of blades; and determining whether the acoustic signature is within an acceptable range.

DETAILED DESCRIPTION OF THE INVENTION

Figure 1:
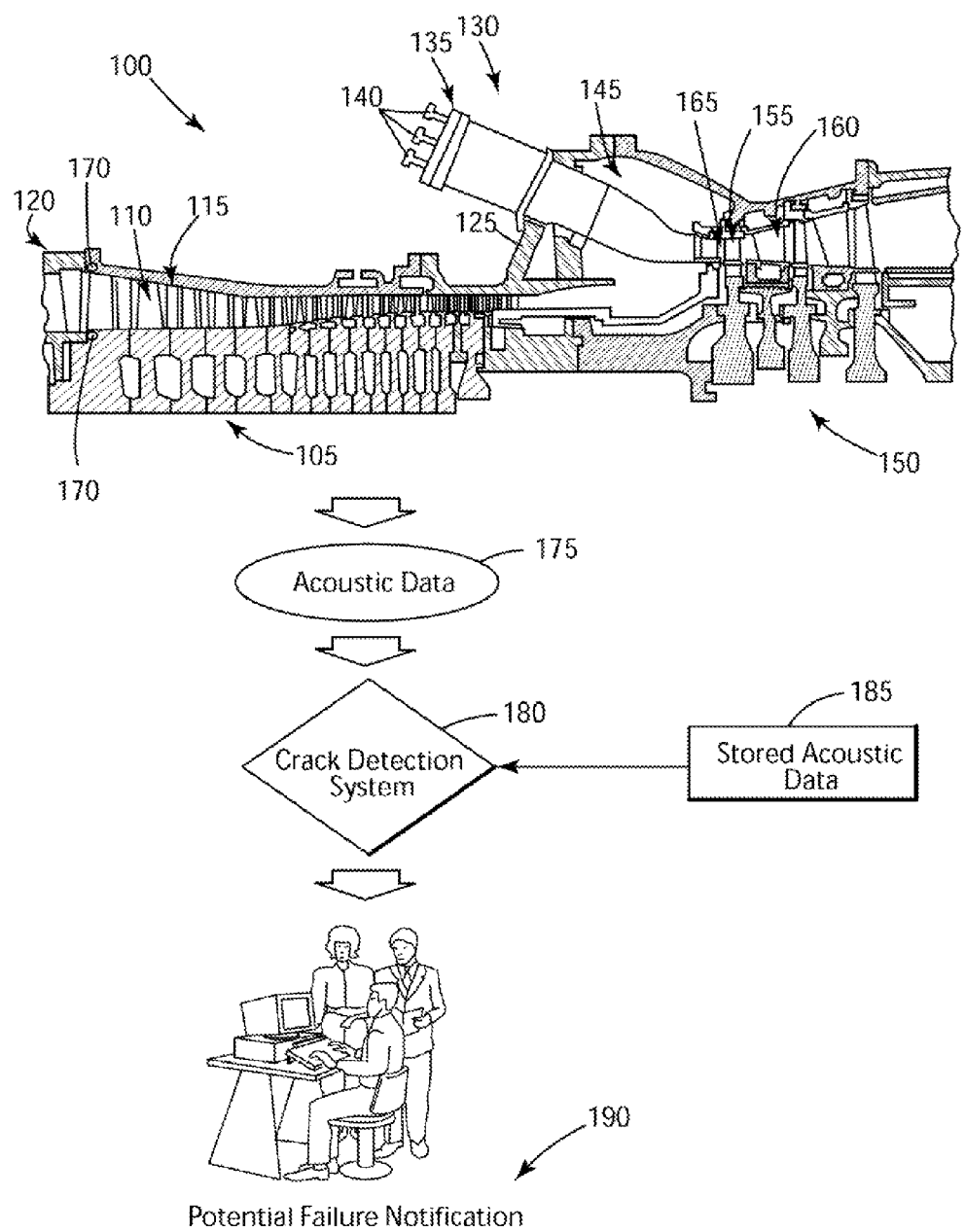
FIG. 1 is a schematic illustrating an environment within which an embodiment of the present invention may operate.

The present invention has the technical effect of monitoring an operating turbomachine for the possibility of a crack on a blade of a turbomachine. The turbomachine may have the form an air-breathing combustion turbine; such as, but not limiting of, a heavy-duty gas turbine, an aero-derivative gas turbine, an aero-engine, other engine comprising a compressor, and the like. Although embodiments of the present invention are described in relation to a gas turbine, application of the present invention is not limited to a gas turbine. Embodiments of the present invention may be applied to other machines that have a plurality of blades, which may not be described herein. In addition, although embodiments of the present invention are described in relation to a blade of a compressor section of a turbomachine application of the present invention is not limited to a turbomachine comprising a compressor section with a plurality of blade. Embodiments of the present invention may be applied to turbomachines not comprising a compressor section, such as, but not limiting of, a steam turbine, or the like.

Detailed example embodiments are disclosed herein. However, specific structural and functional details disclosed herein are merely representative for purposes of describing example embodiments. Example embodiments may, however, be embodied in many alternate forms, and should not be construed as limited to only the embodiments set forth herein.

Accordingly, while example embodiments are capable of various modifications and alternative forms, embodiments thereof are illustrated by way of example in the drawings and will herein be described in detail. It should be understood, however, that there is no intent to limit example embodiments to the particular forms disclosed, but to the contrary, example embodiments are to cover all modifications, equivalents, and alternatives falling within the scope of example embodiments.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments. As used herein, the term "and/or" includes any, and all, combinations of one or more of the associated listed items.

The terminology used herein is for describing particular embodiments only and is not intended to be limiting of example embodiments. As used herein, the singular forms "a", "an" and "the" are intended to include the plural forms as well, unless the context clearly indicates otherwise. It will be further understood that the terms "comprises", "comprising", "includes" and/or "including", when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted might occur out of the order noted in the FIGS. Two successive FIGS., for example, may be executed substantially concurrently or may sometimes be executed in the reverse order, depending upon the functionality/operations involved.

Referring now to the FIGS., where the various numbers represent like parts throughout the several views. FIG. 1 is a schematic illustrating an environment within which an embodiment of the present invention may operate. Embodiments of the present invention may comprise a turbomachine 100, which generates acoustic data 175 that is received by a crack detection system 180. Stored acoustic data 185 may also be sent to the crack detection system 180, which may provide a notification 190 on the possibility of a crack on at least one blade of the compressor section 105.

In FIG. 1, the turbomachine, in the form of a gas turbine 100 includes: a compressor section 105; a combustion system 130; and a turbine section 150. Generally, the compressor section 105 includes a plurality of stationary vanes 110 and rotating blades 115 structured to compress air ingested at the inlet section 125. The compressor section 105 may also include at least one acoustic detection device 170. Here for example, but not limiting of, the acoustic detection device 170 may have the form of a microphone or other sound wave sensing device. Embodiments of the present invention may be applied to a compressor section 105 integrated with a fan or a turbofan section (not illustrated in FIG. 1)

The combustion section 130 may include a plurality of combustion cans 135 (only one is illustrated), a plurality of fuel nozzles 140, and a plurality of transition sections 145 (only one is illustrated). The plurality of combustion cans 135 may be coupled to a fuel source (not illustrated). Within each combustion can 135; compressed air is received from the compressor section 105 and mixed with fuel received from the fuel source. The air and fuel mixture is ignited and creates a working fluid. The working fluid generally proceeds from the aft end of the plurality of fuel nozzles 140 downstream through the transition section 145 into the turbine section 150.

The turbine section 150 may include a plurality of rotating components 155, a plurality of stationary components 160, and a plurality of wheelspace areas 165. Generally, the turbine section 150 converts the working fluid to a mechanical torque used to drive a load (not illustrated).

Figure 2:
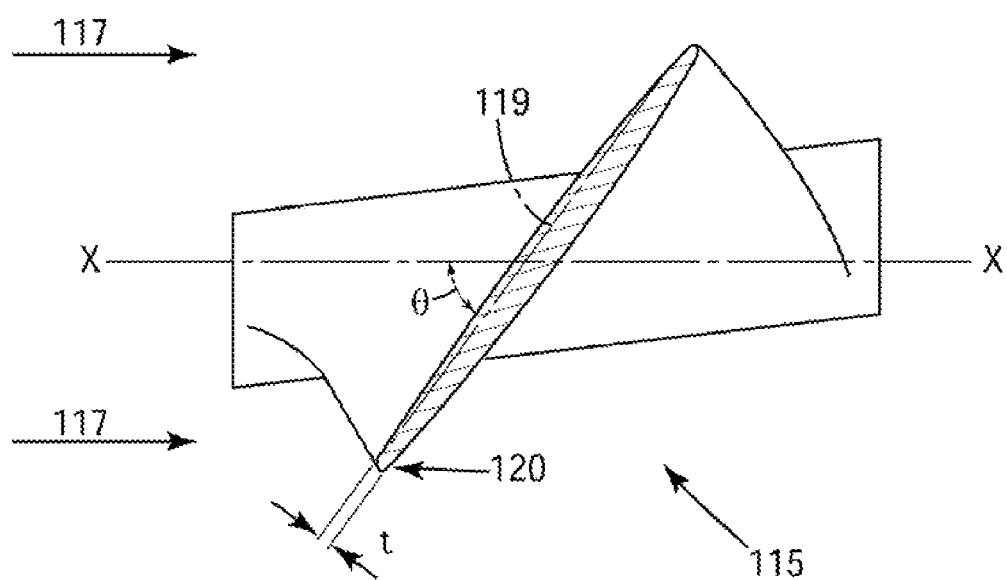
FIG. 2 is a schematic cross-section illustrating an example of a rotating blade of the compressor section illustrated in FIG. 1.

FIG. 2 is a schematic cross-section illustrating an example of a rotating blade 115 of the compressor section 105 illustrated in FIG. 1. FIG. 2 provides general information relating to certain dimensional characteristics of a typical rotating blade 115 within a stage of the compressor section 105. The cross-section illustrates a portion of the rotating blade 115, near the radially outer tip, which experiences sonic or supersonic velocities. The angle θ represents a stagger angle, of the rotating blade 115, at the particular section illustrated. The stagger angle lies between the true chord 119 at that section and the rotational axis X-X of the gas turbine 100. The illustrated "t" represents the thickness at a location 120 and is the leading edge thickness of the section. Location 120 is a location on the rotating blade 115 representative of the blade thickness that engages the air stream 117.

As the rotating blades 115 operate at supersonic tip speeds shock waves are generated. The shock waves are a result of the small differences in the geometry of adjacent rotating blades 115. The shock waves generate an acoustic signature commonly referred to as multiple pure tones (MPT). An MPT acoustic signature is created by acoustic tones produced at integer multiples of the shaft speed. The amplitude of these acoustic tones is unique to the specific stagger angle of each rotating blade 115 within each stage on the compressor section 105.

Embodiments of the present invention provide a method to determining if the stagger angle changes; which may possibly indicate the existence of a crack on the rotating blade 115. Embodiments of the present invention may monitor the MPT signature of the compressor section 105 and automatically detect a change in the MPT signature. This change may indicate that the stagger angle of at least one rotating blade 115 is changing, suggesting that a crack is developing in the rotating blade 115. Embodiments of this method may monitor the compressor section 105 while the gas turbine 100 is operating.

Figure 3:
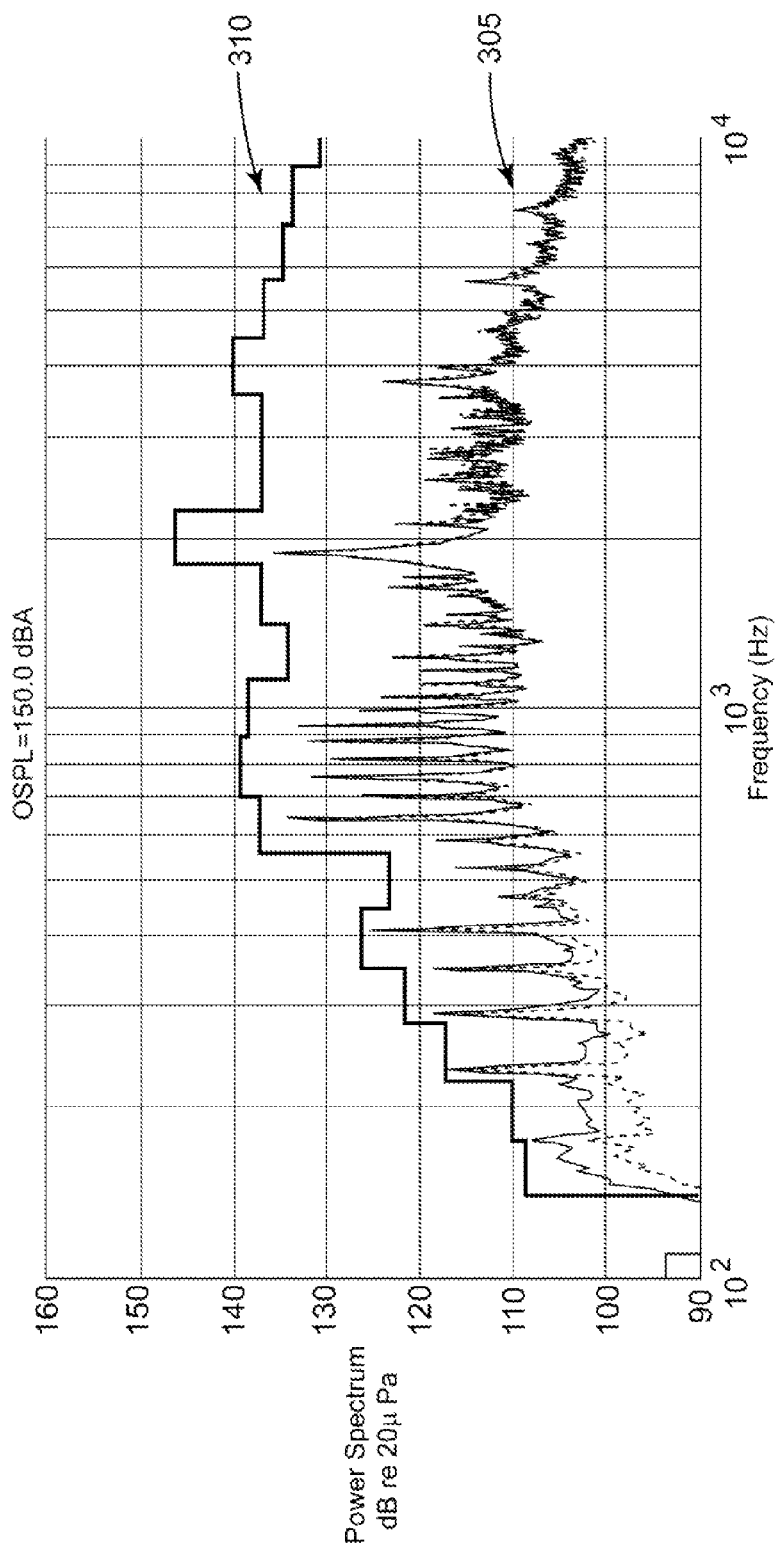
FIG. 3 is a chart illustrating an example of a frequency response curve created in accordance with an embodiment of the present invention.

FIG. 3 is a chart 300 illustrating an example of a frequency response curve created in accordance with an embodiment of the present invention. FIG. 3 illustrates how an MPT may be created in accordance with an embodiment of the present invention. Frequency band amplitude 305 represents the shock wave data captured at a ⅓-octave band level. The acoustic signature 310 represents the shock wave data captured under narrowed spectra of frequency band amplitude. These shock waves may travel upstream through the inlet section 125 and result in the acoustic signature 310. The narrowed spectra of frequency band amplitude associated with a specific acoustic signature 310 may provide narrow band tones most sensitive to stagger angle changes. Frequency band amplitude 305 and the acoustic signature 310 are typically unique to blade-to-blade geometric variations and the stagger angle between the rotating blades 115.

The present invention may create, in real time, a baseline MPT signature for a new or "healthy" gas turbine 100, as the gas turbine 100 operates. Variations from this baseline MPT signature may be indicative of a change in the geometry and stagger angle of the rotating blade 115. As a crack develops, the tip deflection of the rotating blade 115 may change, altering the MPT signature.

As will be appreciated, the present invention may be embodied as a method, system, or computer program product. Accordingly, the present invention may take the form of an entirely hardware embodiment, an entirely software embodiment (including firmware, resident software, micro-code, etc.) or an embodiment combining software and hardware aspects all generally referred to herein as a "circuit", "module," or "system". Furthermore, the present invention may take the form of a computer program product on a computer-usable storage medium having computer-usable program code embodied in the medium. As used herein, the terms "software" and "firmware" are interchangeable, and include any computer program stored in memory for execution by a processor, including RAM memory, ROM memory, EPROM memory, EEPROM memory, and non-volatile RAM (NVRAM) memory. The above memory types are exemplary only, and are thus not limiting as to the types of memory usable for storage of a computer program.

Any suitable computer readable medium may be utilized. The computer-usable or computer-readable medium may be, for example but not limited to, an electronic, magnetic, optical, electromagnetic, infrared, or semiconductor system, apparatus, device, or propagation medium. More specific examples (a non exhaustive list) of the computer-readable medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission media such as those supporting the Internet or an intranet, or a magnetic storage device. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device.

The term processor, as used herein, refers to central processing units, microprocessors, microcontrollers, reduced instruction set circuits (RISC), application specific integrated circuits (ASIC), logic circuits, and any other circuit or processor capable of executing the functions described herein.

Computer program code for carrying out operations of the present invention may be written in an object oriented programming language such as Java7, Smalltalk or C++, or the like. However, the computer program code for carrying out operations of the present invention may also be written in conventional procedural programming languages, such as the "C" programming language, or a similar language. The program code may execute entirely on the user's computer, partly on the user's computer, as a stand-alone software package, partly on the user's computer and partly on a remote computer or entirely on the remote computer. In the latter scenario, the remote computer may be connected to the user's computer through a local area network (LAN) or a wide area network (WAN), or the connection may be made to an external computer (for example, through the Internet using an Internet Service Provider).

The present invention is described below with reference to flowchart illustrations and/or block diagrams of methods, apparatuses (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a public purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable memory. These instructions can direct a computer or other programmable data processing apparatus to function in a particular manner. The such that the instructions stored in the computer-readable memory produce an article of manufacture including instruction means which implement the function/act specified in the flowchart and/or block diagram block or blocks. The computer program instructions may also be loaded onto a computer or other programmable data processing apparatus. These instructions may cause a series of operational steps to be performed on the computer or other programmable apparatus to produce a computer implemented process. Here, the instructions, which execute on the computer or other programmable apparatus, provide steps for implementing the functions/acts specified in the flowchart and/or block diagram blocks.

Figure 4:
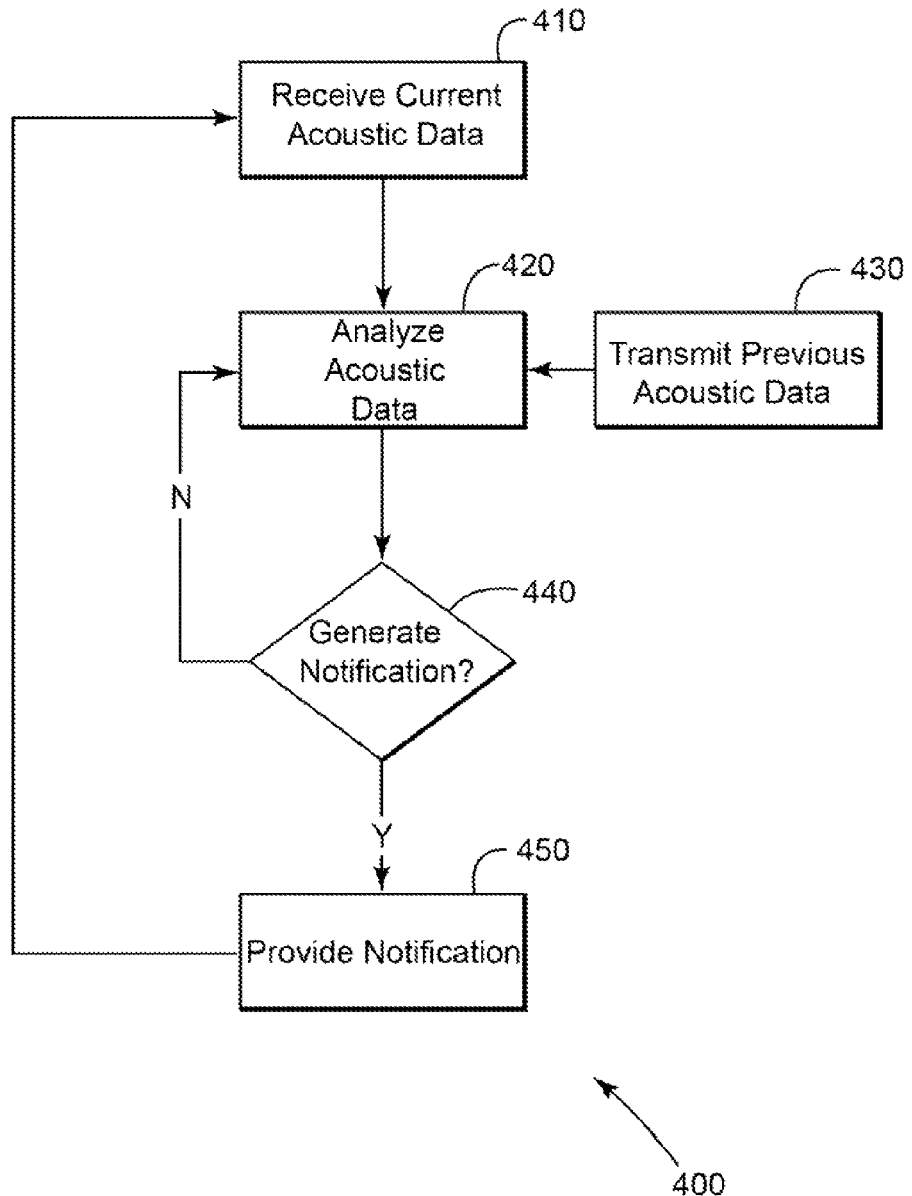
FIG. 4 is a block diagram illustrating a method of monitoring a compressor of a turbomachine, in accordance with an embodiment of the present invention.

Referring again to the FIGS., FIG. 4 is a block diagram illustrating a method 400 of monitoring a compressor of a turbomachine, in accordance with an embodiment of the present invention. In an embodiment of the present invention, an operator may use a control system to monitor or control the operation of the method 400, via a graphical user interface (GUI) or the like.

An embodiment of the method 400 may incorporate at least one algorithm, which may perform the following steps. As discussed, each compressor section 105 may have a unique MPT signature. The algorithm may first establish the baseline MPT signature of the compressor section 105. This step should occur when the compressor section 105 is a new or a "healthy" condition. As the turbomachine 100 operates, the acoustic detection device 170 may constantly monitor the acoustic signature and a processor may then calculate the acoustic frequency spectrum—creating the baseline MPT signature.

Next, the algorithm may compare the real-time MPT signature with a baseline MPT signature. Next, the algorithm may determine the narrowband, or proportional octave, band frequency spectra. Next, the algorithm may determine the individual frequency components. Next, the amplitude of each frequency component may be compared to the amplitude of the corresponding baseline frequency component. Here, if the amplitude of the frequency component begins to deviate by a predetermined threshold level, then an embodiment of the present invention may notify the operator that there is the possibility of a crack developing.

In an embodiment of the present invention, the comparison of the frequency components may occur on a band-by-band basis or by comparing a group of nearby bands. In another embodiment of the present invention, the comparison may include considering a large range of frequencies and detecting changes in the overall spectral shape.

An embodiment of the method 400 may perform the following steps. In step 410, the method 400 may receive the acoustic data from at least one acoustic detection device. In an embodiment of the present invention the acoustic detection device may be located in the inlet section of the compressor section. As described, the acoustic detection device may have the form of a microphone or a sound wave sensing device. The acoustic detection device may be capable of receiving the acoustic data. In addition, the acoustic detection device may be capable of transmitting the acoustic data to the control system, via an electrical signal, or the like.

In step 420, the method 400 may receive the current acoustic data transmitted in step 410. Next an acoustic signature, such as, but not limiting of, a MPT may be created. In an embodiment of the present invention, the method 400 may store the newly created MPT in a local storage device and/or in a remote storage device.

In step 430, the method 400 may transmit previous acoustic data, such as, but not limiting of, a separate MPT to step 420. In an embodiment of the present invention the previous acoustic data may derive from the same gas turbine. Here, the previous acoustic data may serve as the gas turbine baseline. In an alternate embodiment of the present invention, the previous acoustic data may derive from a different gas turbine and/or a fleet of gas turbines. Next, the method 400 may utilize an algorithm that analyzes and compares the MPT signatures from the operating machine and the previous acoustic data transmitted in step 430.

In step 440, the method 400 may determine whether a notification should be generated. In an embodiment of the present invention, the notification may indicate that the current MPT is not within a desired range of the baseline MPT, indicative of a potential crack in a rotating blade. If a notification should be generated, then the method 400 may proceed to step 450; otherwise the method 400 may revert to step 420 where the monitoring process may continue.

In an embodiment of the present invention, the gas turbine may be integrated with a remote monitoring and diagnostic system (RMD). Here, the RMD may receive the acoustic data and may directly contact the operator of the gas turbine, providing a direct notification of a potential crack.

In step 450, the method 400 may generate the notification. Here, the notification may be in the form of an audio and/or visual alarm, or other commonly used communication form.

As discussed, embodiments of the present invention may provide real-time monitoring of the compressor section for the possibility of a crack forming on a rotating blade. The present invention does not require the shutdown of a gas turbine and may be automated to automatically raise an alarm if the acoustic signature of the compressor changes in way that may be consistent with the cracking of a blade.

As one of ordinary skill in the art will appreciate, the many varying features and configurations described above in relation to the several exemplary embodiments may be further selectively applied to form the other possible embodiments of the present invention. Those in the art will further understand that all possible iterations of the present invention are not provided or discussed in detail, even though all combinations and possible embodiments embraced by the several claims below or otherwise are intended to be part of the instant application. In addition, from the above description of several exemplary embodiments of the invention, those skilled in the art will perceive improvements, changes, and modifications. Such improvements, changes, and modifications within the skill of the art are also intended to be covered by the appended claims. Further, it should be apparent that the foregoing relates only to the described embodiments of the present application and that numerous changes and modifications may be made herein without departing from the spirit and scope of the application as defined by the following claims and the equivalents thereof.

What is claimed is:

1. A method of detecting a possible crack on a blade located within a compressor section of a turbomachine, the method comprising:
   operating a turbomachine comprising: a compressor section, wherein the compressor section comprises a plurality of blades; and an acoustic detection device configured for monitoring the compressor section as the turbomachine operates, wherein the acoustic detection device receives acoustic data relating to the plurality of blades;
   utilizing the acoustic data to generate an acoustic signature corresponding to the plurality of blades;
   determining whether the acoustic signature is within an acceptable range; and
   transmitting the acoustic signature to a remote monitoring and diagnostic center;
   wherein a determination that the acoustic signature is outside of the acceptable range indicates a likelihood of a crack on at least one of the plurality of blades.

2. The method of claim 1, wherein the acoustic detection device is located adjacent an inlet section of the compressor section.

3. The method of claim 1 further comprising the step of generating a notification on a result of the step of determining whether the acoustic signature is within an acceptable range.

4. The method of claim 1 further comprising the step of retrieving a related acoustic signature from a storage device.

5. The method of claim 4 further comprising the step of comparing the acoustic signature with a related acoustic signature.

6. The method of claim 5, wherein the related acoustic signature derives from the turbomachine.

7. The method of claim 5, wherein the related acoustic signature derives from at least one different turbomachine.

8. A method of monitoring a turbomachine for a formation of a crack on a blade of the turbomachine, the method comprising:
   operating a turbomachine comprising a plurality of blades; and an acoustic detection device configured for monitoring the turbomachine during operation, wherein the acoustic detection device receives acoustic data relating to the plurality of blades;
   utilizing the acoustic data to generate an acoustic signature corresponding to the plurality of blades;
   comparing the acoustic signature with a related acoustic signature;
   determining whether the acoustic signature is within an acceptable range;
   generating a notification on a result of determining whether the acoustic signature is within an acceptable range of the related acoustic signature; and
   transmitting the acoustic signature to a remote monitoring and diagnostic center;
   wherein a determination that the acoustic signature is outside of the acceptable range indicates that a crack on at least one of the plurality of blades is possible.

9. The method of claim 8 further comprising multiple acoustic detection devices positioned about turbomachine.

10. The method of claim 8 further comprising the step of retrieving the related acoustic signature from a storage device.

11. The method of claim 10 further comprising the step of saving the acoustic signature in the storage device.

12. The method of claim 8, wherein the related acoustic signature derives from the turbomachine.

13. The method of claim 8, wherein the related acoustic signature derives from at least one different turbomachine.

14. A system for detecting an existence of a crack on a blade within a gas turbine, the system comprising:
   a gas turbine comprising a plurality of blades;
   an acoustic detection device configured for monitoring operation of the gas turbine, wherein the acoustic detection device receives acoustic data relating to the plurality of blades and is located adjacent the compressor section;
   a control system, wherein the control system performs the steps of:
      utilizing the acoustic data to generate an acoustic signature corresponding to the plurality of blades; and
      determining whether the acoustic signature is within an acceptable range; and
      transmits the acoustic signature to a remote monitoring and diagnostic center.

15. The system of claim 14, wherein the control system performs the step of comparing the acoustic signature with a related acoustic signature.

16. The system of claim 15 wherein the control system generates a notification on a result on the step of comparing the acoustic signature with the related acoustic signature.

17. The system of claim 15, wherein the related acoustic signature derives from at least one of: the gas turbine; at least one different gas turbine; or a fleet of gas turbines; and wherein related acoustic signature data is received from the remote monitoring and diagnostics center.

18. The system of claim 14 further comprising a plurality of acoustic detection devices located about an inlet section of the compressor section.

* * * * *